United States Patent [19]

Franzblau et al.

[11] Patent Number: 5,489,261
[45] Date of Patent: Feb. 6, 1996

[54] HYDROGELS CAPABLE OF SUPPORTING CELL GROWTH

[75] Inventors: Carl Franzblau, Newton; Barbara A. Faris, Squantum; Linda Civerchia-Perez, Norwood, all of Mass.

[73] Assignee: Trustees of Boston University, Boston, Mass.

[21] Appl. No.: 304,168

[22] Filed: Sep. 12, 1994

Related U.S. Application Data

[60] Continuation of Ser. No. 780,910, Oct. 23, 1991, abandoned, which is a division of Ser. No. 745,874, Jun. 18, 1985, Pat. No. 5,106,743, which is a division of Ser. No. 558,977, Dec. 7, 1983, Pat. No. 4,565,784, which is a continuation of Ser. No. 228,133, Jan. 26, 1981, abandoned.

[51] Int. Cl.$^6$ ..................................................... A61F 13/00
[52] U.S. Cl. ........................................... 602/41; 602/48
[58] Field of Search ........................ 602/41, 42, 43, 602/48, 52, 54; 128/849, 853; 435/240, 240.1, 240.2, 240.21, 240.23, 240.24; 527/201; 524/704, 797; 525/54.1; 530/356

[56] References Cited

U.S. PATENT DOCUMENTS

| | | | |
|---|---|---|---|
| 3,670,731 | 6/1972 | Harmon | 602/42 |
| 4,060,081 | 11/1977 | Yannas et al. | 602/49 |
| 4,061,466 | 12/1977 | Sjoholm et al. | 527/201 |
| 4,193,845 | 5/1976 | Kaetsu et al. | 524/797 |
| 4,248,685 | 2/1981 | Beede et al. | 602/48 X |
| 4,264,155 | 4/1981 | Miyata | 530/356 |
| 4,372,311 | 2/1983 | Potts | 602/48 |
| 4,373,027 | 2/1983 | Berneman et al. | 435/240 |
| 4,388,428 | 6/1983 | Kuzma | 524/704 |
| 4,427,808 | 1/1984 | Stol et al. | 530/356 |
| 4,452,925 | 6/1984 | Kuzma | 527/201 |
| 4,563,490 | 1/1986 | Stol et al. | 530/356 |
| 4,565,784 | 1/1986 | Franzblau et al. | 435/948 |

FOREIGN PATENT DOCUMENTS

| | | | |
|---|---|---|---|
| 0695890 | 10/1964 | Canada | 524/797 |
| 0021379 | 1/1981 | European Pat. Off. | 527/201 |
| 0178217 | 11/1982 | Japan | 527/201 |

OTHER PUBLICATIONS

Chuapil, "Some Chemical and Biological Characteristics of a New Collagen–Polymer Compound Material," JBMR, No. 3 pp. 315–332 (1969).

Civerchia–Perex, et al., Proc. Natl. Acad. Sci. 77(4): 2064–2068 (1980).

*Primary Examiner*—Michael A. Brown
*Attorney, Agent, or Firm*—Hamilton, Brook, Smith & Reynolds

[57] ABSTRACT

A method of growing anchorage-dependent cells is disclosed in which a substrate includes a hydrogel is employed. The hydrogel is formed from an aqueous solution gelled with a crosslinked polymer of a hydrophilic monomer and includes a macromolecule capable of supporting cell growth.

12 Claims, 3 Drawing Sheets

HYDROGELS CAPABLE OF SUPPORTING CELL GROWTH

GOVERNMENT SUPPORT

Work described herein was supported by grants from the National Institutes of Health. This application is a File Wrapper continuation of application Ser. No. 07/780,910 filed Oct. 23, 1991, now abandoned, which is a Divisional of Ser. No. 06/745,874 filed Jun. 18, 1985 and issued as U.S. Pat. No. 5,106,743 on Apr. 21, 1992, which is a Divisional of Ser. No. 06/558,977 filed December 7, 1983 and issued as U.S. Pat. No. 4,565,784 on Jan. 21, 1986, which is a Continuation of Ser. No. 06/228,133 filed Jan. 26, 1981, now abandoned.

Technical Field

This invention is in the field of biology and more particularly relates to cell culturing.

BACKGROUND ART

The ability to grow mammalian cells at the laboratory, clinical and industrial levels is often important. Some mammalian cell types have been adapted for growth in suspension cultures, but other mammalian cell types will grow only if they can become attached to an appropriate surface. The latter cell types are generally termed "anchorage-dependent". Anchorage-dependent cell types include such important cell lines as 3T3 mouse fibroblasts, mouse bone marrow epithelial cells; Murine leukemia virus-producing strains of mouse fibroblasts, primary and secondary chick fibroblasts; WI-38 human fibroblast cells; and normal human embryo lung fibroblast cells.

Anchorage-dependent cells are typically grown in culture vessels such as dishes and flasks. More recently, larger scale propagation of anchorage-dependent mammalian cells has been achieved in roller tubes and roller bottles. In such instances, the anchorage-dependent cells attach to the glass surface of the bottle or to the polymeric material forming the bottom of a culture dish or flask. Nevertheless, it has been found that many common polymeric materials, e.g., polymethyl methacrylate, are unsuitable for cell attachment and growth.

On the other hand, collagen, a natural protein derived from animal sources has long been known to be a substrate capable of promoting cell adhesion and growth. Other proteins are also known to support growth of at least certain cell lines, and it is also known that other macromolecules can support cell growth.

One class of synthetic polymeric materials which have found wide application as biomaterials is the class known as hydrogels. The term "hydrogel" refers to a broad class of polymeric materials which are swollen extensively in water but which do not dissolve in water. Generally, hydrogels are formed by polymerizing a hydrophilic monomer in an aqueous solution under conditions where the polymer becomes crosslinked so that a three-dimensional polymer network sufficient to gel the solution is formed. Hydrogels are described in more detail in Hoffman, A. S., "Polymers in Medicine and Surgery," Plenum Press, New York, pp 33–44 (1974).

Hydrogels have many desirable properties for biomedical applications. For example, they can be made nontoxic and compatible with tissue, and they are usually highly permeable to water, ions and small molecules. Despite these favorable properties, hydrogels have been found, in general, to be unsuitable as substrates for cell attachment and growth. In fact, a hydrogel based upon polyhydroxyethyl methacrylate was employed in one study as a coating on standard tissue culture flasks to prevent fibroblast growth. Folkman, J, and Moscona, A., *Nature* 273, 345–9 (1978).

DISCLOSURE OF THE INVENTION

This invention relates to the growth of anchorage-dependent cells on substrates comprising hydrogels. The hydrogels are formed from aqueous solutions gelled with crosslinked polymers containing a hydrophilic monomer and a macromolecule capable of supporting cell growth. In a preferred case, the hydrophilic monomer is hydroxyethyl methacrylate (HEMA) and the macromolecule capable of supporting cell growth is the protein collagen.

The hydrogels described herein provide substrates capable of supporting good growth of anchorage-dependent cells. Manipulation of cells adhered to the hydrogel surface is feasible, and can have advantages over normal culture surfaces. For example, transfer of cells to another medium or to larger surfaces can be done by simply transferring the hydrogel substrates with their cells attached. Trypsinization to remove cells from a fixed substrate, e.g., bottom of a culture dish, is not required. Additionally, more control over the growth of cells can be obtained since cell growth rate is related to the type and amount of macromolecule present.

These hydrogels can also be employed in the study of various cell growth parameters, as well as the mechanisms of cell adhesion and differentiation, since these hydrogel substrates can be made perfectly transparent so that cell growth can be viewed therethrough. For example, the type and amount of macromolecule added to support cell growth can be varied to study the precise effect of certain macromolecules on cell growth. It is also possible with these hydrogels to create surfaces which can be stretched so that mechanical stress on cells can be evaluated. This might be done by the addition of particular crosslinking agents or by using particular copolymers.

BEST MODE FOR CARRYING OUT THE INVENTION

The hydrogels of this invention differ from those previously produced because of the presence of a macromolecule capable of supporting anchorage-dependent cell growth. Generally, such hydrogels are formed by forming a crosslinked polymer in an aqueous solution to gel the solution. This can be done by free radical polymerization of hydrophilic monomers such as hydroxyethyl methacrylate (HEMA). See, for example, Refojo, M. J. (1965), *J. Appl. Poly. Sci.*, 9, 3416–3426, and Holly, H. and Refojo, M. J. (1975), *J. Biomed. Mat. Res.*, 9, 315. Of course, many other hydrophilic monomers in addition to HEMA can be employed.

One preferred macromolecule added to support cell growth is the protein collagen, a known substrate for good cell growth. Soluble collagen can be prepared by art-recognized techniques. In addition, other proteins are satisfactory as long as they will support cell attachment and growth. An example of an additional protein known to support cell growth is fibronectin.

Macromolecules in addition to proteins can also be added to these hydrogels as long as they are capable of supporting growth of the cells of interest. Polysaccharides are one class of such macromolecules, and those skilled in the art will know others.

Small molecules are not employed because they can diffuse through the hydrogel. Because of the need to anchor or fix the cell supporting molecules, only macromolecules are employed. The macromolecules suitable can be water soluble or insoluble, with the former being preferred.

Crosslinking is often required to form the three dimensional polymeric structure required to gel the aqueous solution. In many cases, sufficient crosslinking is obtained by including a chemical crosslinking agent, such as diacrylates, dimethacrylates, or other divalent molecules. Sometimes, crosslinking agents are already present in the monomer, e.g., hydroxyethyl methacrylate usually contains some dimethacrylate which can serve as a crosslinking agent. Additionally, crosslinking may be done by other techniques such as gamma irradiation or UV irradiation.

The polymerization may be carried out, in situ, that is within the vessel wherein cell growth will occur, or in a separate vessel. In the latter case, sheets of the hydrogel can be cut to an appropriate size and inserted in the cell culture vessel.

It is believed that the macromolecules become trapped within water pockets within the hydrogels. If this is true, and if the cells are not capable of penetrating the hydrogels, then it is only the macromolecules on the surface of the hydrogel which control cell growth. It is possible, therefore, to determine how much macromolecule to incorporate into a particular hydrogel to achieve the desired cell attachment and growth. Those skilled in the art can make such determinations employing the knowledge they possess and no more than routine experimentation.

It might also be possible to rely to some extent upon collagen produced by the growing cells. As previously mentioned, however, fibroblast cells do not grow on HEMA hydrogels, containing no collagen. These particular cells do not produce collagen when grown in the absence of ascorbic acid. Nevertheless, if the proper nutrients are present for cell collagen production, this could lower the amount required in the hydrogels to support cell growth. In fact, it is known that certain cell lines do not produce collagen until they are contacted with collagen, and the hydrogels described herein can be used to cause cells to initiate synthesis of collagen, and possibly other macromolecules.

The growth of a wide variety of anchorage-dependent cells can be supported with the hydrogels of this invention. In general, any anchorage-dependent cell can be studied as long as the hydrogel contains sufficient amounts of a macromolecule to cause the hydrogel to support growth of that particular cell line. Thus, the invention can be used to evaluate the efficacy of certain biological macromolecules to support the adhesion and growth of specific cells in culture.

The invention can be further illustrated by the following examples.

EXAMPLE 1

Preparation of Collagen-Containing Hydrogels

Pepsin soluble collagen was prepared by stirring the ground shaved skin from a one week old calf in 0.5 M acetic acid at 4° C. The residue, after centrifugation, was resuspended in 0.5M acetic acid containing porcine pepsin at a final enzyme-tissue ratio of 1:50 (wet weight) and allowed to stir overnight. The solubilized collagen was then precipitated by addition of solid NaCl to a concentration of 5%. The resulting precipitate was resolubilized in 0.5M acetic acid, then dialyzed exhaustively versus 0.02M $Na_2HPO_4$, pH 7.44 at 4° C. Following dialysis, the precipitate was subjected to differential NaCl precipitation at pH 7.44 as described by Chung and Miller. See Chung, E. and Miller, E. J. (1974), *Science*, 183, 1200–1201. The precipitates were then lyophilized and suspended in 0.5M acetic acid at a concentration of 1.2–1.4 mg/ml as determined by hydroxyproline content, and allowed to stir overnight at 4° C. The resulting solution was dialyzed against 0.15M NaCl-0.05M Tris, pH 7.44, overnight at 4° C. This solution was used as a stock collagen solution.

Polymers of hydroxyethyl methacrylate (HEMA) were essentially prepared by the method of Refojo, Ibid. One ml of commercial HEMA, 1.0 ml of ethylene glycol, 1.0 ml of $H_2O$ or buffer or stock solution of collagen (properly diluted), 0.1 ml of 6% ammonium persulfate and 0.1 ml of 12% sodium metabisulfite were added in sequence. After mixing, the resulting clear viscous monomer solution was polymerized by heating for two hours at 38° C. between two glass slides separated by two coverslips. The approximate thickness of the gel membrane was 0.5 mm. The resulting clear flexible hydrogel membrane was then dialyzed exhaustively versus the Tris-NaCl buffer (pH 7.44) to remove residual monomer and ethylene glycol. During dialysis, the membranes became opaque, but transparency returned once the ethylene glycol had been exchanged for water.

EXAMPLE 2

Cell Growth

Hydrogels prepared as in Example 1 were cut into 1.4 cm diameter buttons and, prior to use in cell cultures, were sterilized in Puck's $Ca^{++}Mg^{++}$ free saline containing 1,000 units penicillin, 50 ug Aureomycin, and 0.25 μg Fungizoine per ml of medium by placing them under ultraviolet lights for two hours. The hydrogels were then transferred to Puck's saline containing penicillin and streptomycin and stored at 4° prior to use.

Figure 1:
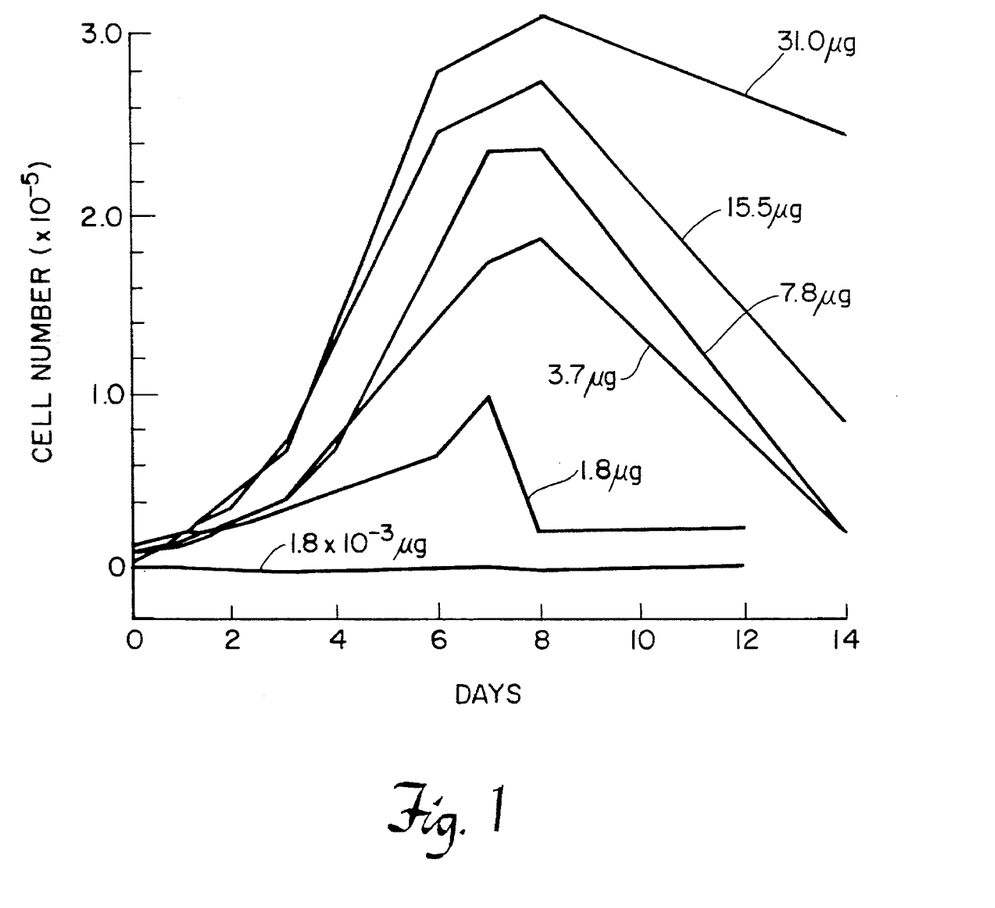
FIG. 1 is a plot of cell number versus time of growth for a series of experiments involving growth of IMR-90 fibroblast cells on HEMA-based hydrogels containing different amounts of collagen.

Human embryonic lung fibroblasts (IMR-90) were used in their 8th passage (23rd population doubling). An individual hydrogel button was placed in each chamber of a cluster dish (24 wells, 1.6 cm diameter). A suspension of cells containing $5 \times 10^4$ cells in 0.5 ml of medium was then added to each chamber. The medium consisted of Dulbecco's Modified Eagle's Medium supplemented by the addition of 10% fetal bovine serum, penicillin (100 units/ml) and streptomycin (100 μg/ml). After the cells had been allowed to settle directly onto the hydrogel button for four hours, the medium in the individual chambers was removed and the buttons were transferred to new chambers which contained 2.0 ml of medium. The number of cells which adhered to the buttons in the initial four-hour period was small relative to the total number of cells suspended. The numbers varied from approximately 4000 cells on those gels with no collagen to 7000–8000 cells on those gels containing collagen. The buttons were then incubated at 37° C in a humidified atmosphere of 5% $CO_2$ and 95% air. Cells were fed three times weekly with 2.0 ml of medium. Cells growing on hydrogels were photographed with a phase contrast microscope at various times. Cell number was determined by transfer of separate hydrogels previously washed with Isoton to a Coulter Counter vial containing 2 ml of 0.05% trypsin in 0.02% EDTA. After five minutes the suspension was vigorously disrupted with a Pasteur pipette in order to prevent cell clumping. The suspension was then diluted to 10 ml with Isoton and counted in the Coulter Counter. Microscopic examination of the hydrogel buttons after such treatment revealed that no cells remained attached to the HEMA gels with or without collagen. Growth of IMR-90 fibreblasts cultured on HEMA hydrogels containing various amounts of collagen was evaluated. Table 1 presents data obtained from these experiments. FIG. 1 presents a graphical presentation of the results of six of these experiments. Each cell number determination is the average of eight individual cultures. The standard deviation in the number of cells within a single time point and at a single collagen concentration was approximately 10%.

TABLE I

| COLLAGEN CONTENT OF HYDROGEL BUTTONS (μg) | MAXIMUM CELL NUMBER ATTAINED ($\times 10^5$) |
| --- | --- |
| 31.0 | 3.09 |
| 24.0 | 3.10 |
| 16.0 | 2.74 |
| 8.0 | 2.89 |
| 6.0 | 2.48 |
| 4.0 | 1.89 |
| 2.0 | 1.56 |
| 0.9 | 0.52 |
| 0.3 | 0.19 |
| 0.2 | 0.13. |

It can be seen that hydrogels prepared with HEMA and buffer only were unfavorable surfaces for supporting fibroblast growth. In general, there was a correlation between increased cell number and higher percentages of collagen in the hydrogel.

Figure 2:
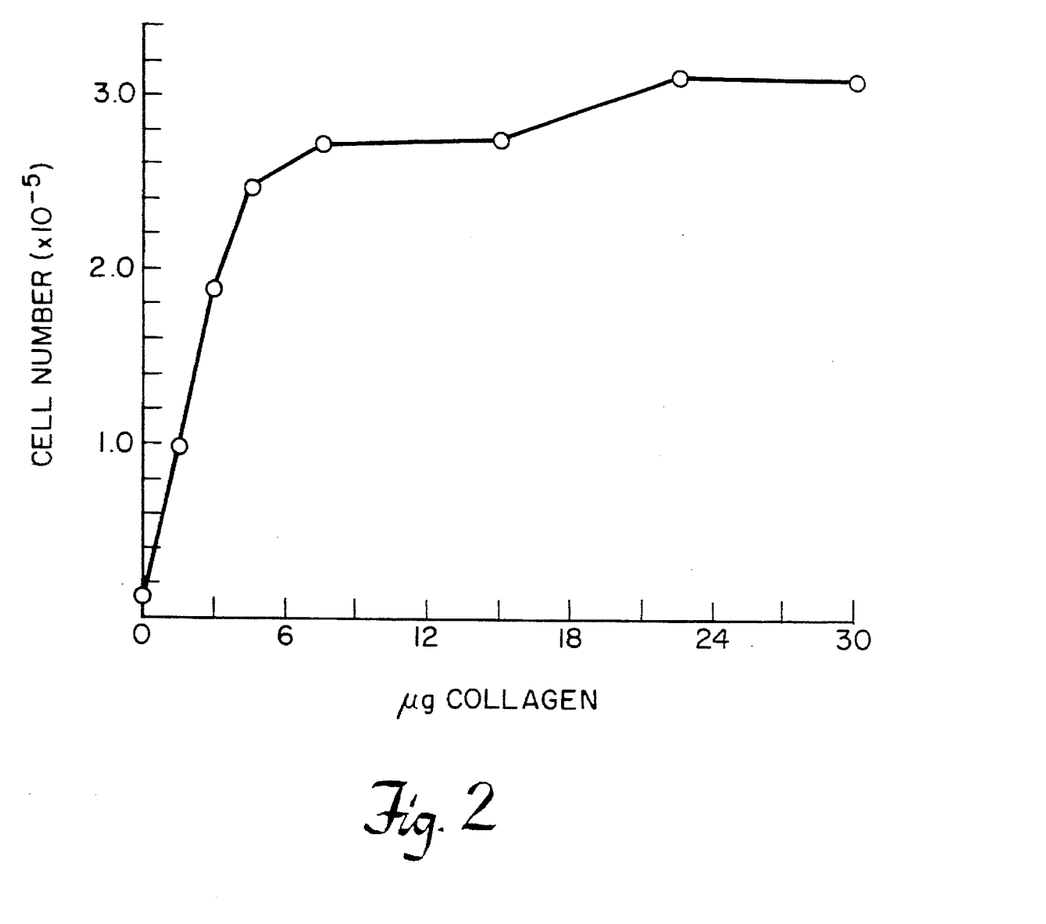
FIG. 2 is a plot of maximal cell growth obtained vs. collagen content for a series of experiments involving growth of IMR-90 fibroblast cells on HEMA-based hydrogels containing different amounts of collagen.
Figure 3:
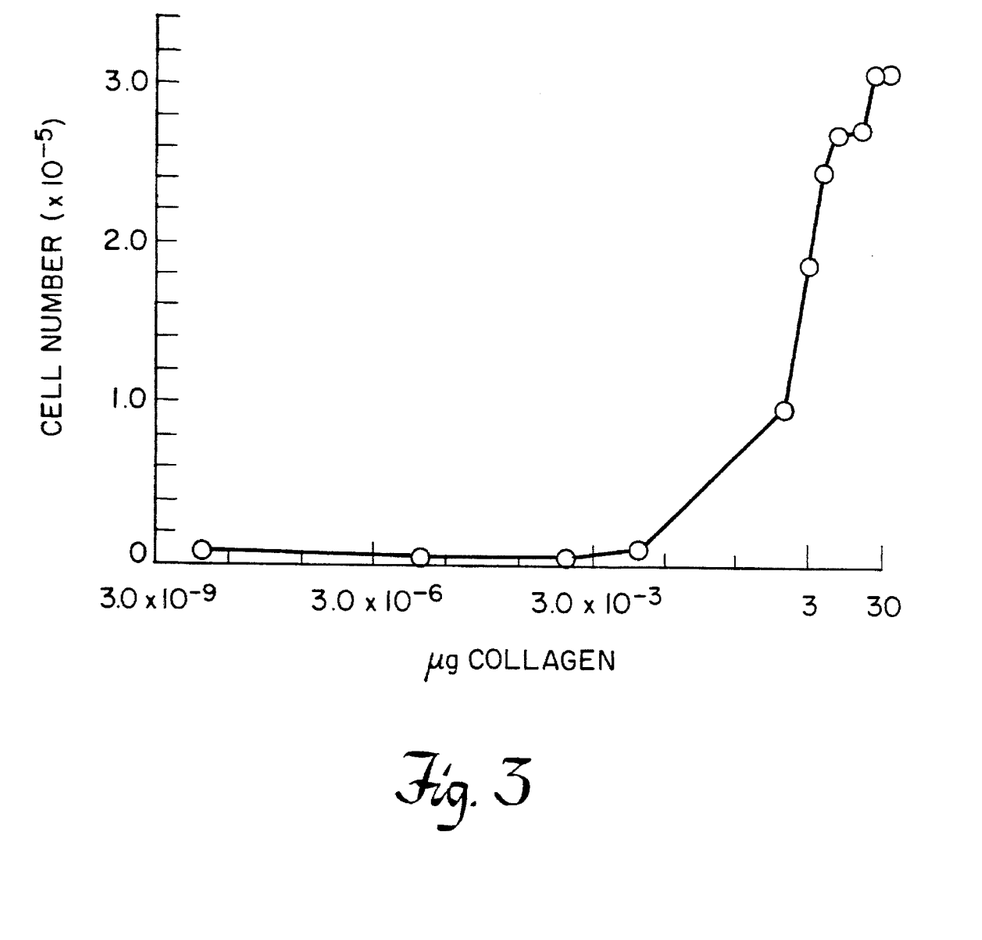
FIG. 3 is a plot of maximal cell growth obtained vs. collagen content, on a logarithmic scale, for a series of experiments involving growth of IMR-90 fibroblast cells on HEMA-based hydrogels containing different amounts of collagen.

FIGS. 2 and 3 were plotted to show the effect of varying concentrations of collagen in the hydrogels as a function of the maximum obtainable cell number. The maximum cell number obtained was employed regardless of the day on which this occurred. Hydrogels which marginally supported cell growth displayed cell "sluffing" earlier than those gels displaying maximal cell growth. The content of collagen in the hydrogel preparation which was capable of supporting approximately 80% of maximum cell number observed was 16 μg. The minimum collagen content of a hydrogel button necessary to detect any significant cell growth was 0.2 μg.

EXAMPLE 3

Hydrogels-Containing Albumin

Hydrogels containing albumin were prepared following the procedure of Example 1, except that albumin was added in place of collagen. Bovine serum albumin obtained from Sigma Chemical Co. was employed.

Cell cultures were formed following the procedures of Example 2 with these albumin-containing hydrogels. The albumin-containing hydrogels did support cell growth but not as well as those hydrogels containing collagen.

EXAMPLE 4

Treatment of Hydrogels with Collagenase

Prior to antibiotic treatment for cell culturing, certain of the hydrogel buttons containing collagen (Example 1) and albumin (Example 3) were incubated individually with 20 ug of purified bacterial collagenase in 0.5 ml of 0.15M NaCl-0.05M Tris, 0.036 mM $CaCl_2$, pH 7.5, for 20 hours at room temperature with shaking. Bacterial collagenase (Clostridium histolyticum) Type I was purchased from Sigma Chemical Co. and further purified by Sephadex G-200 gel filtration as described by Peterkofsky. See Peterkofsky, B. and Diegelmann, R. (1971), *Biochem.*, 10, 988–994. The collagenase was assayed as described by Hu et al. See Hu, C. L., Crombie, G.1 and Franzblau, C. (1978), *Anal. Biochem.*, 88, 638–643. After treatment with collagenase, the buttons were treated with 2.0 ml of 0.5M EDTA solution for 15 minutes, washed with Tris-NcCl buffer and prepared for cell culture as described above.

Enzymatic incubation did not appear to alter the gross physical integrity of the hydrogel membranes. However, treatment of collagen-containing hydrogels with the purified bacterial collagenase eliminated cell growth. The cell number on these hydrogels was the same as the number of cells on hydrogels which contained no collagen. Morphologically, cells grown on the HEMA-collagen hydrogels which were incubated with collagenase appeared round and sparsely distributed similar to cells grown on hydrogels without protein. The albumin hydrogels treated with collagenase did not support cell growth as well as the collagen hydrogels, with the maximum cell number on the albumin hydrogels being the same whether treated with collagenase or not.

EXAMPLE 5

Hydroxyproline Analyses of Protein Hydrogels

Membranes prepared with collagen-containing hydrogels, as described in Example 1, were finely minced to increase surface area and hydrolyzed in vacuo in 6N HCl at 110° C. for 20 hours. The HEMA membrane itself did not dissolve under these conditions and, therefore, analyses were easily performed on the supernatant of these membranes employing a Beckman Model 119-CL Amino Acid analyzer. Collagen content could be estimated on the basis of hydroxyproline content of the hydrolysate. For comparison, hydrogels containing collagen were minced and treated with bacterial collagenase as described in Example 4 and then hydrolyzed in 6N HCl. Control hydrogels were incubated with buffer as described above, but without enzyme. The control and collagenase supernatants were hydrolyzed and amino acid analyses were performed on all samples.

Hydrolysates of collagen-containing hydrogels yielded amino acid analyses consistent with that of collagen. However, all of the collagen was not recovered from the hydrogel by hydrolysis in 6N HCl which suggests that the collagen incorporated into the hydrogel was tightly bound and not readily accessible to hydrolysis. Approximately 32% of the hydroxyproline added to the hydrogel was recovered after hydrolysis.

In the experiments wherein bacterial collagenase was used to solubilize the collagen in the hydrogels, no hydroxyproline was detected in the supernatant. This suggests that the collagenous material originally incorporated into the hydrogel might be covalently bound or entrapped within the hydrogel structure and not susceptible to the action of the bacterial collagenase. In this vein, the interior collagen is most likely not accessible to the cells adhered to the surface of the hydrogels since the HEMA gel is not easily penetrated by the cells.

EXAMPLE 6

Comparison Between Growth of Cells On Hydrogels and Plastic Dishes

Hydroxyethyl methacrylate (HEMA) hydrogels were prepared by mixing sequentially, 1.0 ml of HEMA, 1.0 ml of ethylene glycol, 1.0 ml of 0.05M tris-0.16M NaCl buffer, pH 7.4, 0.1 ml of 6% ammonium persulfate and 0.1 ml of 12% sodium metabisulfite. For the collagen-HEMA hydrogels used, 1.0 ml of a pepsin extracted calf skin collagen solution which contained 0.6 mg collagen in the tris-NaCl buffer was substituted for the buffer. The hydrogels were polymerized by heating for two hours at 38° C. between two glass slides separated by two cover slips. The resulting gels were approximately 0.5 mm thick. The gels were dialyzed exhaustively versus tris-NaCl buffer to remove residual monomer and ethylene glycol. After dialysis, the gels were cut into 1.4 cm diameter buttons with a size 10 cork borer. The buttons were sterilized in Puck's $Ca^+$—$Mg^+$ free saline G containing 1000 units penicillin, 50 µg achromycin, and 0.25 µg fungizone per ml by placing them under ultraviolet light for 2 hours. They were subsequently transferred to Puck's saline containing 100 units/ml of penicillin and 100 µg/ml of streptomycin.

Cultures were prepared with human embryonic lung fibroblasts (IMR-90) at the 9th–11th passages (population doubling level (PDL) 24–26). The medium used was Essential Modified Eagle's Medium supplemented by the addition of 10% newborn calf serum, 1 mM sodium pyruvate, penicillin (100 units/ml) and streptomycin (100 µg/ml). An individual hydrogel button was placed into each chamber of a cluster dish (24 wells, 1.6 cm diameter). Prior to cell plating, the buttons were incubated for 1 hour at 37° C. in 1 ml of serum-free Essential Modified Eagle's Medium. This was then removed and 0.5 ml of complete medium containing $5\times10^4$ cells was added to the chambers containing gels as well as to chambers without gels. After a 4 hour incubation at 37°, the buttons were removed to new chambers which contained 2.0 ml of media. In the case of the cells plated onto the wells, the media was removed and two ml fresh media was added to each well. The dishes were subsequently incubated at 37° C. in a humidified atmosphere of 5% $CO_2$ and 95% air and fed three times weekly with 2 ml of medium.

Cells were photographed regularly under a phase contrast microscope. To determine the cell number on the buttons, each gel was rinsed with isoton, transferred to a Coulter Counter vial containing 2 ml of 0.05% trypsin in 0.02% EDTA and incubated at 37° C. for 10 minutes. The suspension was then diluted to 10 ml with isoton and agitated vigorously with a pipette in order to remove all the cells from the gels before counting in the Coulter Counter. The cells grown directly on the wells were harvested by washing the cell layer twice with Puck's saline and adding two ml of trypsin-EDTA. This was followed by incubation for ten minutes at 37° C., dispersion with a pasteur pipette, and removal of the cell suspension to a Coulter Counter vial. Six individual hydrogels or chambers were counted and averaged to determine the cell number at each time point.

Cells were also harvested from hydrogels and wells and replated onto standard tissue culture surfaces. In this case, the cell layers on the two surfaces were rinsed and then incubated with Puck's saline for 15 minutes prior to treatment with 2.0 mls of trypsin-EDTA in the chambers. After the standard 10 minute incubation at 37° C., the cells were disrupted with a pipette and removed to a centrifuge tube containing media. The two cell suspensions were spun at 800 rpm for 10 minutes and the pellets were resuspended in media to give a final cell suspension of $5\times10^4$ cells/0.5 ml. The cells were then plated onto tissue culture wells as above.

Electron microscopy was performed by removing the culture medium from the hydrogels or tissue culture wells and the cell layers were rinsed twice with 4.3% glutaraldehyde in 0.1M Veronal buffer, pH 7.4, and subsequently kept in the same solution for one hour at room temperature. The cultures were then rinsed with buffer, and post-fixed with 1% $OsO_4$ in 0.075M Veronal buffer for 30 minutes at room temperature. Those cells seeded on tissue culture wells were dehydrated in a graded series of ethanol solutions and embedded in a 1:1 mixture of Araldite 502 and dodecyl succinic anhydride. The dehydration and embedding procedures for cells seeded on hydrogels were modified to minimize hydrogel swelling and shrinking, and to facilitate infiltration of the Araldite mixture into the hydrogel. The hydrogels were initially dehydrated in 70% and 80% ethanol solutions containing 0.15M NaCl, followed by the standard dehydration in 95% and 100% ethanol. Infiltration of the cells and the periphery of the hydrogel with the Araldite mixture was achieved by placing the hydrogel-Araldite mixture overnight in a vacuum oven at 40° C. After polymerization, thin sections were cut in a plane perpendicular to the flask or hydrogel growing surface with an LKB Ultratome V, stained with uranyl acetate and lead citrate, and examined with a Philips 300 Electron Microscope.

$^{14}$C-Proline pulsing was performed six days after plating by removing the medium from each chamber after which the cell layers on either the plasticware or hydrogels were washed with 1.0 ml of proline-free medium containing 50 ug sodium ascorbate per ml. The cells were incubated for 1 hour in this medium which was then replaced with 1.0 ml of the same medium containing 2 µCi of $^{14}$C-proline (sp. act. 294.0 mCi/mmole; New England Nuclear). After a 24 hour incubation, the medium was removed and the cell layers washed with 0.9% NaCl. The media and NaCl washes were pooled, centrifuged to remove any debris, dialyzed to remove free $^{14}$C-proline, and lyophilized. Cell layers grown directly on the wells were harvested in phosphate buffered saline, pH 7.4, by scraping the cells from the wells with the aid of a rubber policeman. The resulting cell suspensions were then dialyzed and lyophilized. In the case of the cells grown on gels the intact gel with cells was removed, dialyzed and lyophilized. In each set of experiments, the media and cell layers from a minimum of 12 gels or wells were analyzed for $^{14}$C-hydroxyproline and $^{14}$C-proline content. These were pooled in groups of 4 gels or wells after harvesting.

The presence of $^{14}$C-hydroxyproline and $^{14}$C-proline in the lyophilized medium and cell fractions was determined by hydrolyzing each sample in 6N HCl at 110° C. for 20 hours and then analyzing the hydrolysates on a Beckman amino-acid analyzer with a stream-splitting arrangement. The radioactivity in aliquots of the column eluant was monitored in a Packard Tri-carb liquid scintillation spectrometer.

The results are presented in Tables II–IV below:

TABLE II

IMR FIBROBLAST GROWTH (CELL NUMBER) ON HEMA-COLLAGEN GELS

| Time | †Blank Gels | *Hema-Collagen Gels | Tissue Culture Wells |
|---|---|---|---|
| 4 hrs | 4,700 | 15,400 | 29,100 |
| 2 days | 1,600 | 35,235 | 56,680 |
| 4 days | 1,600 | 146,290 | 170,700 |
| 6 days | 1,900 | 124,750 | 335,670 |
| 8 days | | 148,470 | 359,530 |

†HEMA gels without protein
*Approximately 20 ug collagen per HEMA gel

TABLE III

IMR-90 FIBROBLAST GROWTH (CELL NUMBER) ON TISSUE CULTURE SURFACE AFTER SUB-CULTIVATION FROM EITHER HEMA-COLLAGEN HYDROGELS OR TISSUE CULTURE WELLS

| Time | From Gels | From Wells |
|---|---|---|
| 4 hours | 27,900 | 24,000 |
| 2 days | 54,700 | 44,200 |
| 3 days | 66,500 | 60,900 |
| 6 days | 147,200 | 122,300 |
| 8 days | 218,000 | 197,500 |

TABLE IV

COLLAGEN SYNTHESIS BY IMR-90 ON COLLAGEN-HEMA GELS OR IN WELLS
Population Doubling 25

| | CPM HYDROXYPROLINE/100,000 CELLS | | |
|---|---|---|---|
| | GELS | WELLS | GELS/WELLS |
| Cell Layer | 5,300 | 5,300 | 1.0 |
| | 6,900 | 4,970 | 1.4 |
| Medium | 9,500 | 4,700 | 2.0 |
| | 16,735 | 10,325 | 1.6. |

Table II shows that cells attained a higher final number on the tissue culture chambers than on the collagen hydrogels. The standard deviation in the number of cells within a single time point is approximately 15%. When cell growth figures were corrected for differences in area of the hydrogel buttons (1.4 cm diameter) and the wells (1.6 cm diameter), the rate of growth on the two surfaces-was nearly identical through the first four days. Between the fourth and eighth days, the cell number on the gels remained fairly constant while the cells on the tissue culture wells continued to grow, finally reaching a plateau between the sixth and seventh day. It was difficult to distinguish grossly between the two cell populations under a phase microscope, both appearing confluent. Layering of cells was more evident in the wells although layering occurred on both surfaces. This layering of cells was also evident when electron microscopy was performed on the cell layers from the two surfaces. An electron micrograph of cells grown on either surface demonstrated the cell layer to be at least three cells deep.

Table III indicates that the cells from the two surfaces do not differ significantly in their growth pattern when subcultivated in tissue culture chambers. Thus, while the cells on the hydrogels did not attain as high a density as those on tissue culture surfaces, they were capable, after subcultivation, of the same growth as those cells which Were never exposed to collagen hydrogels.

The production of radioactive hydroxyproline was employed to monitor collagen synthesis in the medium and cell layer fractions from the pulsed cells grown on the collagen-hydrogels or in the wells. Table IV compares the $^{14}$C-hydroxyproline present in cultures of cells grown on the collagen-hydrogels or tissue culture surfaces on a per cell basis. The $^{14}$C-hydroxyproline associated with the insoluble cell layer fractions is approximately the same regardless of the surface the cells were grown on. However, 1.6–2.0 times as much $^{14}$C-hydroxyproline is present in the soluble proteins of the medium fraction from those cells grown on collagen hydrogel surfaces when compared to cells grown in wells.

The percent hydroxylation, when measured by radioactivity, is approximately 26% in each medium fraction regardless of the surface the cells were grown on or the age of the cells. Similarly, the percent hydroxylation in the insoluble cell fraction is 5–6% in all cases. These data suggest that while the total amount of collagen synthesized by cells grown on collagen hydrogels or tissue culture surfaces may differ, the percent collagen in the newly synthesized protein is always the same.

EXAMPLE 7

Growth of Cultured Rabbit Pulmonary Artery Smooth Muscle Cells on Protein Hydrogels Cells grown on hydroxyethyl methacrylate hydrogels (HG) containing collagen or fibronectin were studied. The procedures of Examples 1 and 2 were employed for hydrogel preparation and cell growth.

When seeded on (HG) containing no protein, cells appeared to attach after 4 hours but became rounded and detached within 24 hours. With low collagen or fibronectin concentrations in the (HG), cells attached and divided but did not become confluent. Instead they tended to cluster and detach. At high concentrations of collagen or fibronectin, cells formed a confluent layer. The increase in cell number occurring on these (HG) was very similar to that on plasticware. After reaching confluency, areas of the cell layer tended to pull together to form clusters, and detached with time. The detachment time-appeared to be (HG) protein concentration dependent; the more protein present, the slower the clustering. Interestingly, cell growth did not occur on (HG) that had had cells which subsequently detached. It is concluded that cell growth on (HG) containing collagen or fibronectin is dependent on surface protein concentration and that the cell-hydrogel interaction appears to be actively involved in controlling cell-cell interactions.

Industrial Applicability

This invention has industrial applicability in the culturing of anchorage-dependent cells as well as in the clinical and laboratory study of the parameters affecting cell growth.

Equivalents

Those skilled in the art will recognize other equivalents to the specific materials and/or steps described herein, and these equivalents are intended to be encompassed by the claims attached hereto.

We claim:

1. A wound dressing comprising a single layer hydrogel formed from an aqueous solution gelled with a crosslinked polymer of a hydrophilic monomer and having incorporated within said hydrogel a cell growth-supporting macromolecule in an amount sufficient to render the hydrogel capable of supporting growth of anchorage-dependent mammalian cells.

2. A wound dressing comprising a single-layer hydrogel formed from an aqueous solution gelled with a crosslinked polymer of a hydrophilic monomer and having incorporated within said single-layer hydrogel a cell growth-supporting macromolecule in an amount sufficient to render the single-layer hydrogel capable of supporting growth of anchorage-dependent mammalian cells.

3. The wound dressing of claim 2, wherein the cell growth-supporting macromolecule is collagen.

4. The wound dressing of claim 2, wherein the cell growth-supporting macromolecule is albumin.

5. A wound dressing comprising a one layer hydrogel having incorporated therein a cell growth-supporting macromolecule, the hydrogel formed by a method comprising the steps of:

a) combining a polymer of a hydrophilic monomer and the cell-growth supporting macromolecule in an aqueous solution; and b) crosslinking the polymer to gel the aqueous solution, thereby forming a hydrogel, wherein the macromolecule is incorporated within the hydrogel.

6. A wound dressing comprising a one-layer hydrogel having incorporated therein a cell growth-supporting macromolecule, the one-layer hydrogel formed by a method comprising the steps of:

a) combining a polymer of a hydrophilic monomer and the cell-growth supporting macromolecule in an aqueous solution; and b) crosslinking the polymer to gel the aqueous solution, thereby forming the one-layer hydrogel, wherein the macromolecule is incorporated within the one-layer hydrogel.

7. The wound dressing of claim 6, wherein the cell growth-supporting macromolecule is collagen.

8. The wound dressing of claim 6, wherein the cell growth-supporting macromolecule is albumin.

9. A wound dressing which is a one layer hydrogel formed from an aqueous solution gelled with a crosslinked polymer of a hydrophilic monomer and having incorporated within said hydrogel a cell growth-supporting macromolecule in an amount sufficient to render the hydrogel capable of supporting growth of anchorage-dependent mammalian cells.

10. A wound dressing which includes a one-layer hydrogel formed from an aqueous solution gelled with a crosslinked polymer of a hydrophilic monomer and having incorporated within said one-layer hydrogel a cell growth-supporting macromolecule in an amount sufficient to render the one-layer hydrogel capable of supporting growth of anchorage-dependent mammalian cells.

11. The wound dressing of claim 10, wherein the cell growth-supporting macromolecule is collagen.

12. The wound dressing of claim 10, wherein the cell growth-supporting macromolecule is albumin.

* * * * *

UNITED STATES PATENT AND TRADEMARK OFFICE
CERTIFICATE OF CORRECTION

PATENT NO. : 5,489,261
DATED : February 6, 1996
INVENTOR(S) : Carl Franzblau, Barbara A. Faris and Linda Civerchia It is certified that error appears in the above-indentified patent and that said Letters Patent is hereby corrected as shown below:

Column 10 - 11
Delete Claim 1.
Renumber Claim 2 as Claim 1.
Insert New Claim 2:
--2. The wound dressing of Claim 1, wherein the hydrophilic monomer is hydroxyethyl methacrylate.--
Claim 3, line 1, delete "2" and substitute therefor --1--.
Claim 4, line 1, delete "2" and substitute therefor --1--.
Delete Claim 5.
Re-number Claim 6 as Claim 5.
After re-numbered Claim 5, insert as new Claim 6:
--6. The wound dressing of Claim 5, wherein the hydrophilic monomer is hydroxyethyl methacrylate.--

Col. 12,
Claim 7, line 1, delete "6" and substitute therefor --5--

Claim 8, line 1, delete "6" and substitute therefor --5--

UNITED STATES PATENT AND TRADEMARK OFFICE
CERTIFICATE OF CORRECTION

PATENT NO. : 5,489,261
DATED : February 6, 1996
INVENTOR(S) : Carl Franzblau, Barbara A. Faris and Linda Civerchia It is certified that error appears in the above-indentified patent and that said Letters Patent is hereby corrected as shown below:

Column 12,
Delete Claim 9.
Re-number Claim 10 as Claim 9.
After re-numbered Claim 9, insert as new Claim 10:
--10. The wound dressing of Claim 9, wherein the hydrophilic monomer is hydroxyethyl methacrylate.--
Claim 11, line 1, delete "10" and substitute therefor --9--.
Claim 12, line 1, delete "10" and substitute therefor --9--.

Signed and Sealed this

Twentieth Day of May, 1997

Attest:

BRUCE LEHMAN

*Attesting Officer*  *Commissioner of Patents and Trademarks*